(12) United States Patent
Ishizuka et al.

(10) Patent No.: US 7,163,933 B2
(45) Date of Patent: Jan. 16, 2007

(54) TREATING AGENT FOR PAGET'S DISEASE OF BONE

(75) Inventors: Seiichi Ishizuka, Hino (JP); Kazuya Takenouchi, Hino (JP); Atsushi Imaizumi, Tokyo (JP); Yasuhiro Oue, Hino (JP); Noriyoshi Kurihara, Pittsburgh, PA (US); Sakamuri V. Reddy, Pittsburgh, PA (US); G. David Roodman, Pittsburgh, PA (US)

(73) Assignee: Teijin Limited, Osaka (JP)

( * ) Notice: Subject to any disclaimer, the term of this patent is extended or adjusted under 35 U.S.C. 154(b) by 510 days.

(21) Appl. No.: 10/369,752

(22) Filed: Feb. 21, 2003

(65) Prior Publication Data

US 2003/0191094 A1   Oct. 9, 2003

Related U.S. Application Data

(63) Continuation-in-part of application No. 10/079,890, filed on Feb. 22, 2002, now abandoned.

(51) Int. Cl.
    *A61K 31/59* (2006.01)
(52) U.S. Cl. .................................................. 514/167
(58) Field of Classification Search ............... 514/167
    See application file for complete search history.

(56) References Cited

U.S. PATENT DOCUMENTS 4,857,518 A   8/1989  DeLuca et al.
5,583,125 A   12/1996 Steinmeyer et al.
5,719,297 A   2/1998  Tabe et al.

FOREIGN PATENT DOCUMENTS

| DE | 197 10 054 A1 | 9/1998 |
| DE | 197 44 127 A1 | 4/1999 |
| EP | 1 123 921 A1 | 8/2001 |
| WO | WO 02/15894 A2 | 2/2002 |

OTHER PUBLICATIONS

Thavarajah et al., Biochemical and Biophysical Research Communications, 1990 ;171(3) :1056-1063.*

S.D. Neale, et al., "Osteoclast Differentiation From Circulating Mononuclear Precursors in Paget's Disease Is Hypersensitive to 1,25-Dihydroxyvitamin $D_3$ and RANKL," Bone, Sep. 2000, pp. 409-416, vol. 27, No. 3, Pergamon Press, Oxford, GB.

D. Somjen, et al., "A non-calcemic analog of $1\alpha,25$ dihydroxy vitamin $D_3$ (JKF) upregulates the induction of creatine kinase B by $17\beta$ estradiol in osteoblast-like ROS 17/2.8 cells and in rat diaphysis," The Journal of Steroid Biochemistry & Molecular Biology, Jun. 2001, pp. 205-212, vol. 77, No. 4/5, Elsevier Science Ltds., Oxford, GB.

Andrea Toell, et al., "Different Molecular Mechanisms of Vitamin $D_3$ Receptor Antagonists," Molecular Pharmacology, 2001, pp. 1478-1485, vol. 59, No. 6.

(Continued)

*Primary Examiner*—San-Ming Hui
(74) *Attorney, Agent, or Firm*—Sughrue Mion, PLLC

(57) ABSTRACT

To obtain a treating agent for Paget's disease of bone, there is provided a method of inhibiting expression of general transcription factor of steroid hormone receptor.

10 Claims, 2 Drawing Sheets

OTHER PUBLICATIONS

Michaela Herdick, et al., "Antagonistic Action of a 25-Carboxylic Ester Analogue of 1α,25-Dihydroxyvitamin $D_3$ Is Mediated by a Lack of Ligand-induced Vitamin D Receptor Interaction with Coactivators," The Journal of Biological Chemistry, Jun. 2, 2000, pp. 16506-16512, vol. 275, No. 22.

Yvonne Bury, et al., "Structure Activity Relationship of Carboxylic Ester Antagonists of the Vitamin $D_3$ Receptor," Molecular Pharmacology, Nov. 2000, pp. 1067-1074, vol. 58, No. 5.

Michaela Herdick, "Carboxylic ester antagonists of 1α,25-dihydroxyvitamin $D_3$ show cell-specific actions," Chemistry & Biology, 2000, pp. 885-894, vol. 7, No. 11.

Tanja Gaschott, "Butyrate-Induced Differentiation of Caco-2 Cells Is Mediated by Vitamin D. Receptor," Biochemical and Biophysical Research Communications, 2001, pp. 690-696, vol. 288, No. 3, Academic Press, Inc., Orlando, Florida.

T. Suda, "Modulation of Osteoclast Differentiation by Local Factors," Bone, Aug. 1, 1995, pp. 87S-91S, vol. 2, No. 17, Pergamon Press, Oxford, GB.

S. Patel, et al., "Drugs Used in the Treatment of Metabolic Bone Disease Clinical Pharmacology and Therapeutic Use," Adis International Limited, 1993, pp. 594-617, vol. 46, No. 4.

N. Kurihara, et al., "Identification of Committed Mononuclear Precursors for Osteoclast-Like Cells Formed in Long Term Human Marrow Cultures", Endocrinology, vol. 126, No. 5, pp. 2733-2741.

Rowena D. Devlin, et al., "Alterations in Vitamin D Metabolites During Treatment of Paget's Disease of Bone with Calcitonin or Etidronate", Journal of Bone and Mineral Research, vol. 5, No. 11, 1990, pp. 1121-1126.

Noriyoshi Kurihara, et al., "Osteoclasts expressing the measles virus nucleocapsid gene display a pagetic phenotype", The Journal of Clinical Investigation, Mar. 2000, vol. 105, No. 5, pp. 607-614.

Gabrielle Mengus, et a., "Cloning and characterization of $hTAF_{II}18$, $hTAF_{II}20$ and $hTAF_{II}28$: three subunits of the human transcription factor TFIID", The EMBO Journal, 1995, vol. 14, No. 7, pp. 1520-1531.

Michaela Herdick, et al., "Antagonistic Action of a 25-Carboxylic Ester Analogue of 1α,25-Dihydroxyvitamin $D_3$ Is Mediated by a Lack of Ligand-induced Vitamin D Receptor Interaction with Coactivators", The Journal of Biological Chemistry, Jun. 2, 2000, vol. 275, No. 22, pp. 16506-16512.

Rowena A. Devlin, et al., "Long-Term Elevation of 1,25-Dihydroxyvitamin D After Short-Term Intravenous Administration of Pamidronate (*Aminohydroxypropylidene bisphosphonate*, APD) in Paget's Disease of Bone", Journal of Bone and Mineral Research, 1994, vol. 9, No. 1, pp. 81-85.

Cheikh MenaA, et al., "I,25-Dihydroxyvitamin $D_3$ Hypersensitivity of Osteoclast Precursors from Patients with Paget's Disease", Journal of Bone and Mineral Research, No. 2, 2000, vol. 15, pp. 228-236.

Ethel S. Siris, "Paget's Disease of Bone", Primer on the Metabolic Bone Diseases and Disorders of Mineral Metabolism, Department of Medicine, The University of Chicago Medical Center, Chapter 77, pp. 415-425.

Daishiro Miura, et al., "Antagonistic Action of Novel 1α,25-Dihydroxyvitamin $D_3$-26,23-lactone Analogs on Differentiation of Human Leukemia Cells (HL-60) Induced by 1α,25-Dihydroxyvitamin $D_3$", The Journal of Biological Chemistry, Jun. 4, 1999, vol. 274, No. 23, pp. 16392-16399.

Keiichi Ozono, et al., Analysis of the Molecular Mechanism for the Antagonistic Action of a Novel 1α,25-Dihydroxyvitamin $D_3$ Analogue toward Vitamin D Receptor Function , The Journal of Biological Chemistry. Nov. 5, 1999. vol. 274, No. 45, pp. 32376-32381.

Yamada et al., Steroids, 2001 ; 66: 177-187.

\* cited by examiner

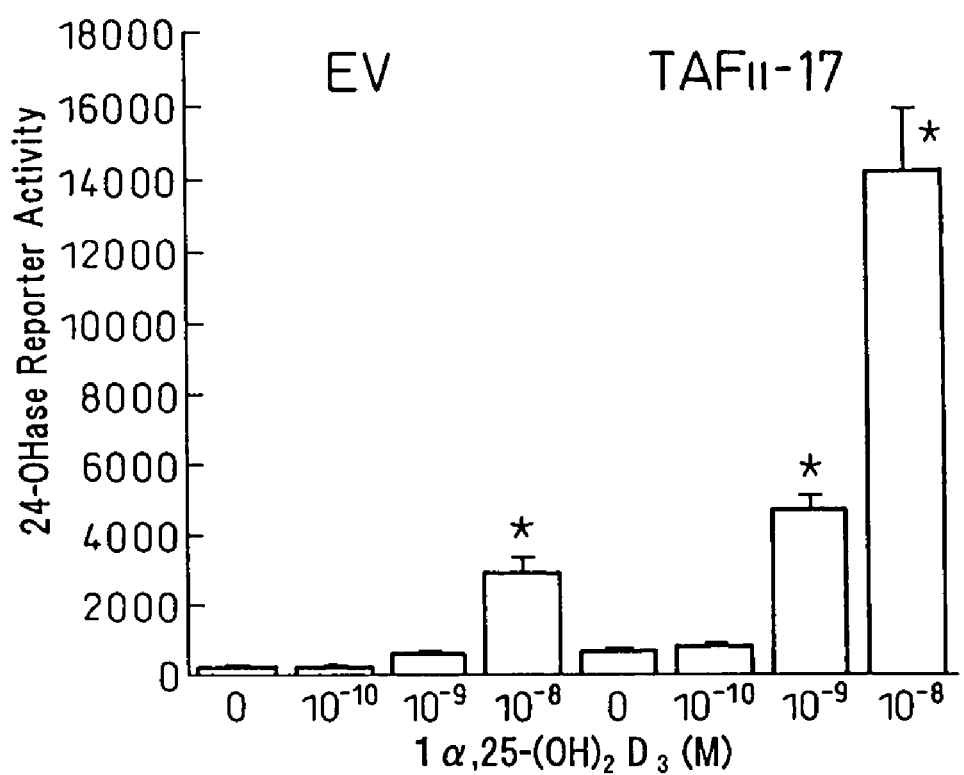

SEQUENCE LISTING

```
<160> NUMBER OF SEQ ID NOS: 15

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Leu Met Gly Leu Leu
 1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Leu Leu Ser Leu Leu
 1               5

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Leu Ile Ser Leu Leu
 1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Leu Glu Ser Leu Leu
 1               5
```

```
<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Leu Tyr Pro Leu Leu
 1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Leu Trp Gly Leu Leu
 1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Leu Trp Ser Leu Leu
 1               5

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Leu Met Lys Leu Leu
 1               5

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Leu Gly Gly Leu Leu
 1               5

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 10

Leu Glu Gln Leu Leu
 1               5

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Leu Leu Lys Leu Leu
 1               5

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Leu Glu Arg Leu Leu
 1               5

<210> SEQ ID NO 13
<211> LENGTH: 160
<212> TYPE: PRT
<213> ORGANISM: Homo sapiens

<400> SEQUENCE: 13

Met Asn Gln Phe Gly Pro Ser Ala Leu Ile Asn Leu Ser Asn Phe Ser
 1               5                  10                  15

Ser Ile Lys Glu Pro Ala Ser Thr Pro Pro Gln Gly Ser Met Ala Asn
             20                  25                  30

Ser Thr Ala Val Val Lys Ile Pro Gly Thr Pro Gly Ala Gly Gly Arg
         35                  40                  45

Leu Ser Pro Glu Asn Asn Gln Val Leu Thr Lys Lys Lys Leu Gln Asp
     50                  55                  60

Leu Val Arg Glu Val Asp Pro Asn Glu Gln Leu Asp Glu Asp Val Glu
 65                  70                  75                  80

Glu Met Leu Leu Gln Ile Ala Asp Asp Phe Ile Glu Ser Val Val Thr
                 85                  90                  95

Ala Ala Cys Gln Leu Ala Arg His Arg Lys Ser Ser Thr Leu Glu Val
            100                 105                 110

Lys Asp Val Gln Leu His Leu Glu Arg Gln Trp Asn Met Trp Ile Pro
        115                 120                 125

Gly Phe Gly Ser Glu Glu Ile Arg Pro Tyr Lys Lys Ala Cys Thr Thr
    130                 135                 140

Glu Ala His Lys Gln Arg Met Ala Leu Ile Arg Lys Thr Thr Lys Lys
145                 150                 155                 160

<210> SEQ ID NO 14
<211> LENGTH: 32
<212> TYPE: DNA
<213> ORGANISM: Artificial Sequence
<220> FEATURE:
<223> OTHER INFORMATION: Description of Artificial Sequence: Primer
```

```
-continued

<400> SEQUENCE: 14
cagccatggc tatgaaccag tttggcccct ca                                32

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 15
atactgcagt tatttcttgg ttgttttccg                                   30
```

US 7,163,933 B2

TREATING AGENT FOR PAGET'S DISEASE OF BONE

This is a Continuation-In-Part of U.S. application Ser. No. 10/079,890, filed Feb. 22, 2002; now abandoned the above noted prior application is hereby incorporated by reference.

TECHNICAL FIELD

The present invention relates to the use of therapeutic agents for Paget's disease of bone, containing a compound which inhibits expression of general transcription factor of steroid hormone receptor as their active moiety. In addition, the present invention provides a method for screening a compound for treatment of Paget's disease of bone.

BACKGROUND ART

A bone tissue is a dynamic tissue in which breaking and formation are continuously repeated. The breaking, i.e. resorption of bone and succeeding bone formation collectively constitute a phenomenon called remodeling, and through the remodeling, the bone tissue is continuously reconstructed throughout life. If the balance between bone resorption and bone formation is destroyed, various kinds of metabolic bone diseases are developed. When bone resorption exceeds bone formation, bone mass gradually decreases. Typical diseases in this case are osteomalacia and osteoporosis.

A disease whose bone resorption is more accelerated than osteoporosis is Paget's disease of bone. The cause of Paget's disease of bone is not known yet; however, a fingerprint like pattern of the osteoclast nucleus of Paget's disease of bone suggests that the disease is caused by virus. In a patient with Paget's disease of bone, bone metabolism turnover is extremely active on disease sites, and the disease often develops on pelvises, femurs, skulls, cervical vertebrae, vertebrae, clavicles, humeri or the like. An osteoclast activated to the utmost has an extremely large size, contains a number of nuclei and performs active bone resorption. When the restoration by osteoblasts is activated to the utmost, lamellar bones and bone trabeculae having coarse net shapes and large thickness are formed. Even in the case of dense calcification, mosaic layered collagen forms weak bone which is structurally fat (Primer on the Metabolic Bone Diseases and Disorders of Mineral Metabolism, fourth edition, p. 415–425, 1999, Lippincott Williams & Wilkins).

Recently, it has become clear that osteoclast precursor cells and osteoclasts collected from patients with Paget's disease of bone have $1\alpha,25$-dihydroxyvitamin $D_3$ receptors, and the sensitivity to $1\alpha,25$-dihydroxyvitamin $D_3$ of the osteoclast precursor cells and osteoclasts were 10 to 100 times larger than the sensitivity of osteoclast precursor cells and osteoclasts collected from normal adults (J. Bone Miner. Res., vol. 15, 228–236 (2000)). Further, it has been reported that serum of patients with Paget's disease of bone contains $1\alpha,25$-dihydroxyvitamin $D_3$ at a concentration same as that of normal adults (50–150 pM; 20–60 pg/ml serum) (J. Bone Miner. Res., vol. 5, 1121–1126 (1990) and J. Bone Miner. Res., vol. 9. 81–85 (1994)). This shows that in osteoclast precursor cells of normal adults, osteoclast formation is virtually not induced by $1\alpha,25$-dihydroxyvitamin $D_3$ of physiological concentration and, on the contrarily, in osteoclast precursor cells collected from patients with Paget's disease of bone, the osteoclast formation is stimulated in the presence of $1\alpha,25$-dihydroxyvitamin $D_3$ of physiological concentration, and bone resorption is accelerated. Furthermore, it was reported that when nucleocapsid genes of measles viruses are transduced into osteoclast precursor cells of normal adults, and $1\alpha,25$-dihydroxyvitamin $D_3$ solution of physiological concentration is made to act on the cells, osteoclasts having a shape completely identical to the osteoclasts collected from patients with Paget's disease of bone are formed, and they actively perform bone resorption (J. Clin. Invest. vol. 105, 606–614 (2000)). The above findings suggest that the rapid acceleration of bone resorption observed in the patients with Paget's disease of bone is attributable to the acceleration of osteoclast formation and the activation of the formed osteoclasts caused by the enhancement of the sensitivity to $1\alpha,25$-dihydroxyvitamin $D_3$ of osteoclast precursor cells with measles virus infection.

In patients with Paget's disease of bone, the acceleration of sensitivity to $1\alpha,25$-dihydroxyvitamin $D_3$ is observed only on the bone in which the bone resorption has been stimulated, and thereby, it seems that the abnormalities of the disease exist in osteoclast precursor cells and osteoclasts. Further, judging from the fact that the sensitivity to $1\alpha,25$-dihydroxyvitamin $D_3$ is accelerated at least 100 times more that of normal adults, it is difficult to consider that the cause of the acceleration of the sensitivity is attributable to the increase of the number of vitamin D receptors and the increase of the binding constant of vitamin D receptor to $1\alpha,25$-dihydroxyvitamin $D_3$, and accordingly it is presumed that "coactivator", that is, a transcription factor to a vitamin D receptor in an osteoclast precursor cell and an osteoclast of a patient with Paget's disease of bone is expressed. If this presumption is correct, a compound suppressing such an expression of a transcription factor may be useful as a treating agent for Paget's disease of bone and to become a treating agent which is more fundamental and useful compared with a bone resorption suppressor, such as a bisphosphonate preparation and a calcitonin preparation, which is presently used.

SUMMARY OF THE INVENTION

The inventors of the present invention closely studied the mechanism of action regarding the enhancement of the sensitivity to $1\alpha,25$-dihydroxyvitamin $D_3$ of osteoclast precursor cells from patients with Paget's disease of bone and the acceleration of bone resorption caused by the enhancement of the sensitivity. As a result, they made clear that in osteoclast precursor cells and osteoclasts from patients with Paget's disease of bone, a transcription factor, TATA box-binding protein-associated factor II-17 (TAFII-17, this factor was already reported as various names such as hTAFII20 (The EMBO Journal vol. 14, 1520–1531 (1995)), TAF20/15 (J. Biol. Chem., 271, 18194–18202 (1996)) and hTAF12 (GENE & DEVELOPMENT 16, 673–675 (2002)), TAFII-135 or vitamin D receptor-interacting protein-205 (DRIP-205) is expressed, and thereby the sensitivity to $1\alpha,25$-dihydroxyvitamin $D_3$ is enhanced. These factors were not detected in above mentioned cells from normal volunteers. That is to say they are Paget's disease specific factors. They also found that when the expression of the transcription factor is suppressed, the enhancement of the sensitivity to $1\alpha,25$-dihydroxyvitamin $D_3$ disappears and the acceleration of bone resorption is suppressed. Further, they found compounds having suppressing activity on the expression of the transcription factor. Based on these findings, it has become clear that compounds having suppressing activity on the expression of the transcription factor are useful as a treating agent for Paget's disease of bone.

The purpose of the present invention is to provide a method for treating Paget's disease of bone by suppressing the expression of the transcription factor to steroid hormone receptor.

In addition, the present invention provides a method for screening a compound for treatment of Paget's disease of bone, comprising the step of detecting TAFII-17, TAFII-135 or DRIP-205 gene expression. More specifically, the step of detecting TAFII-17, TAFII-135 or DRIP-205 gene expression comprises the steps of:

(a) incubating a compound to be tested with mononuclear cells prepared from bone mallow collected from a patient with Paget's disease of bone;

(b) extracting RNA from the cells from step (a);

(c) converting the RNA of step (b) into cDNA and amplifying TAFII-17, TAFII-135 or DRIP-205 gene by, for example, polymerase chain reaction; and (d) fractionating and determining the TAFII-17, TAFII-135 or DRIP-205 gene of step (c) by, for example, electrophoresis.

BRIEF EXPLANATION OF DRAWINGS

FIG. 2 shows 25-hydroxyvitamin $D_{3-24}$-hydrohylase (24-OHase) reporter assay in TAFII-17 gene transfected NIH3T3 cells.

DETAILED DESCRIPTION OF THE PREFERRED EMBODIMENTS

Figure 1:
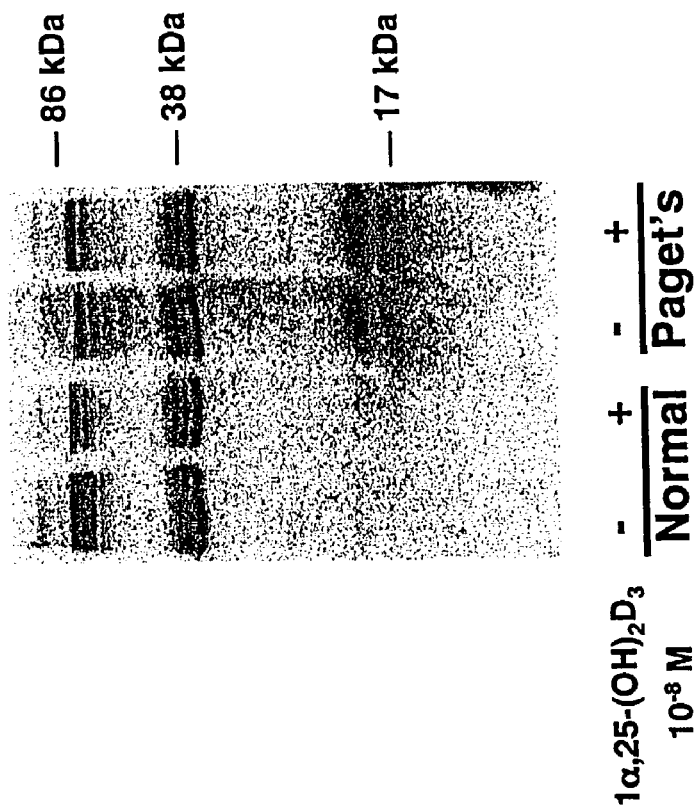
FIG. 1 shows separation of Vitamin D receptor (VDR) associated nuclear proteins from bone marrow mononuclear cells of normal adult and patient with Paget's disease by SDS-polyacrylamide gel electrophoresis.

The transcription factor includes, for example, TATA box-binding protein-associated factor II-17 (TAFII-17), TAFIT-135, DRIP-205.

The hormone receptor includes a receptor which is able to regulate the expression of the transcription factor. Among them is preferable vitamin D receptor (VDR) or retinoid X receptor (RXR).

Samples of the compounds which have interactive relation to vitamin D receptor and suppressive effect of expression the transcription factor include compounds expressed by the following formula (1), Among formula (1), a compound whose m is 1 or 2 is preferable. Further, regarding the combinations of m, q, r and X, compounds shown in Table 1 are preferable; and among them, compounds No. 11, 13, 16, 21, 23 and 26 are especially preferable. In the compounds shown in Table 1, if an asymmetric carbon is present in the structure, it includes both the (S) and (R) configurations.

TABLE 1

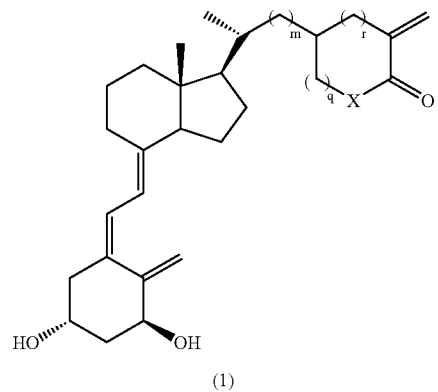

(1)

| Compound No. | m | q | r | X |
|---|---|---|---|---|
| 11 | 1 | 0 | 1 | oxygen |
| 12 | 1 | 1 | 1 | oxygen |
| 13 | 1 | 0 | 1 | carbon |
| 14 | 1 | 0 | 2 | carbon |
| 15 | 1 | 0 | 3 | carbon |
| 16 | 1 | 1 | 0 | carbon |
| 17 | 1 | 2 | 0 | carbon |
| 18 | 1 | 3 | 0 | carbon |
| 21 | 2 | 0 | 1 | oxygen |
| 22 | 2 | 1 | 1 | oxygen |
| 23 | 2 | 0 | 1 | carbon |
| 24 | 2 | 0 | 2 | carbon |
| 25 | 2 | 0 | 3 | carbon |
| 26 | 2 | 1 | 0 | carbon |
| 27 | 2 | 2 | 0 | carbon |
| 28 | 2 | 3 | 0 | carbon |

In addition, samples of the compounds which have interactive relation to vitamin D receptor and suppressive effect of expression the transcription factor include compounds expressed by the following formula (2),

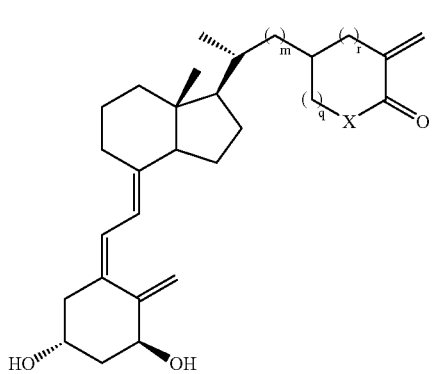

(1)

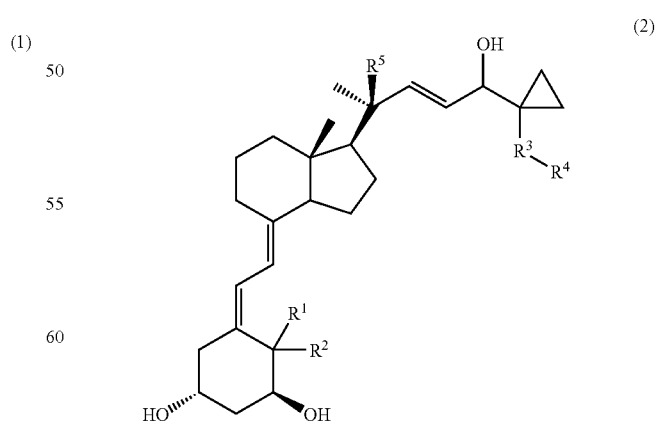

(2)

[in formula (1), m is an integer selected from 1 to 3; q is an integer selected from 0 to 3; r is an integer selected from 0 to 3; X is carbon or oxygen; and $1 \leq q+r \leq 3$]

[in formula (2), $R^1$ and $R^2$ are each hydrogen or they together form an exocyclic methylene; $R^3$ is a single bond, methylene or vinylene; $R^4$ is a normal or branched $C_1$ to $C_7$ alkylcarbonyl, alkenylcarbonyl, alkoxycarbonyl or alkylaminocarbonyl; phenyl, 2-oxazolyl or 2-thiazolyl which may be substituted with a $C_1$ to $C_6$ alkyl; $R^5$ is hydrogen or methyl].

Among formula (2), compounds shown in Table 2 are preferable. In the compounds shown in Table 2, if an asymmetric carbon is present in the structure, the compounds include both the (S) and (R) configurations. When $R^3$ is vinylene, the configuration of the double bond includes both (E)-configuration and (Z)-configuration.

TABLE 2

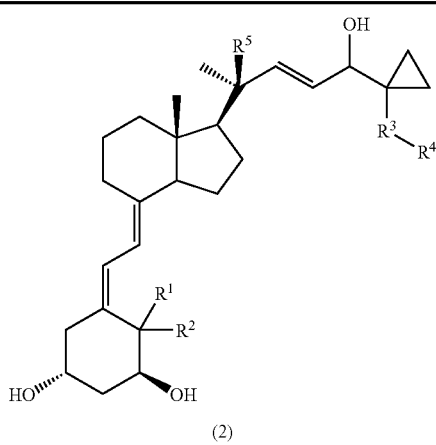

(2)

| Compound No. | $R^1$ | $R^2$ | $R^3$ | $R^4$ | $R^5$ |
|---|---|---|---|---|---|
| 31 | exocyclic methylene | | single bond | n-butoxy-carbonyl | hydrogen |
| 32 | exocyclic methylene | | single bond | 2-methyl-propoxy-carbonyl | hydrogen |
| 41 | exocyclic methylene | | single bond | n-butyl-carbonyl | hydrogen |
| 42 | exocyclic methylene | | single bond | n-pentyl-carbonyl | hydrogen |
| 43 | exocyclic methylene | | single bond | n-heptyl-carbonyl | hydrogen |
| 44 | exocyclic methylene | | single bond | 1-pentenyl-carbonyl | hydrogen |
| 51 | exocyclic methylene | | single bond | n-butyl-aminocarbonyl | hydrogen |
| 52 | exocyclic methylene | | single bond | n-pentyl-aminocarbonyl | hydrogen |
| 53 | exocyclic methylene | | single bond | n-heptyl-aminocarbonyl | hydrogen |
| 54 | exocyclic methylene | | single bond | 1-pentenyl-aminocarbonyl | hydrogen |
| 61 | exocyclic methylene | | single bond | 2-(5-butyl) oxazolyl | hydrogen |
| 71 | exocyclic methylene | | single bond | 2-(5-butyl) thiazolyl | hydrogen |
| 72 | exocyclic methylene | | single bond | 2-(4-methyl) thiazolyl | hydrogen |
| 73 | exocyclic methylene | | single bond | 2-(4-propyl) thiazolyl | hydrogen |
| 81 | exocyclic methylene | | vinylene | ethoxy-carbonyl | hydrogen |
| 82 | exocyclic methylene | | vinylene | t-butoxy-carbonyl | hydrogen |
| 91 | hydrogen | hydrogen | single bond | n-butoxy-carbonyl | hydrogen |
| 101 | hydrogen | hydrogen | vinylene | ethoxycarbonyl | hydrogen |

The compounds of the present invention can be synthesized by a method described in the description of international patent publications WO 95/33716 (Compounds of formula (1)), WO 00/24712 (Compounds of formula (1)), WO 94/07853 (Compounds of formula (2)), WO 97/00242 (Compounds of formula (2)) and WO 97/041096 (Compounds of formula (2)). Compounds of formula (1) directly suppress the effects of 1α,25-dihydroxyvitamin $D_3$ by inhibiting the binding between 1α,25-dihydroxyvitamin $D_3$ and a 1α,25-dihydroxyvitamin $D_3$ receptor (VDR) (J. Biol. Chem., vol. 274, 16392–16399 (1999)), the binding between VDR and a 9-cis-retinoic acid receptor (RXR), and the binding between VDR and a steroid receptor coactivator 1 (SRC-1) of a transcription factor (J. Biol. Chem., vol. 274, 32376–32381 (1999). Compounds of formula (2) appear to antagonize the action of 1α,25-dihydroxyvitamin $D_3$ (J. Biol. Chem., vol. 275, 16506–16512 (2000)).

Samples of the compounds which have interactive relation to retinoid X receptor and suppressive effect of expression the transcription factor include the various RXR antagonist, for example, LXXLL peptide (J. Bone Miner. Res., Vol. 17, 2196–2205 (2002)) and diazepinylbenzoic acid derivative (Chem. Pharm. Bull., vol. 47, 1778–1786 (1999)).

Regarding the LXXLL peptide, L is leucine and X is any amino acid. Among the peptide, the following combination of XX amino acids are preferable: -methionine-glycine- (SEQ ID NO: 1), -leucine-serine- (SEQ ID NO: 2), -isoleucine-serine- (SEQ ID NO: 3), -glutamic acid-serine- (SEQ ID NO: 4), -tyrosine-proline- (SEQ ID NO: 5), -tryptophane-glycine- (SEQ ID NO: 6), -tryptophane-serine- (SEQ ID NO: 7), -methionine-lysine- (SEQ ID NO: 8), -glycine-glycine- (SEQ ID NO: 9), -glutamic acid-glutamine- (SEQ ID NO: 10), -leucine-lysine- (SEQ ID NO: 11) or glutamic acid-arginine- (SEQ ID NO: 12). (These substitutions in the LXXLL peptide are shown in SEQ ID NOS 1–12).

Treating agents of the present invention can be administered orally, or through a parental route such as intravenous, subcutaneous, intramuscular, intranasal or intrarectal route.

Dosage forms for oral administration include tablets, pills, powders, granules, liquids, suspensions, syrups, capsules, etc.

The tablets are formulated according to a conventional process by using additives consisting of an excipient such as lactose, starch, calcium carbonate, crystalline cellulose or silicic acid; a binder such as carboxymethylcellulose, methylcellulose, calcium phosphate or polyvinylpyrrolidone; a disintegrator such as sodium alginate, sodium bicarbonate, sodium laurylsulfate or stearic acid monoglyceride; a wetting agent such as glycerin; an absorbent such as kaolin or colloidal silica; a lubricant such as talc or granular boric acid, etc.

The pills, powders and granules are prepared by conventional processes also using additives similar to those mentioned above.

Liquid preparations such as solutions, suspensions and syrups can be formulated also according to conventional processes. As a carrier, for example, a glycerol ester such as tricaprylin, triacetin or an iodized poppy oil fatty acid ester; water; an alcohol such as ethanol; or en oily base such as liquid paraffin, coconut oil, soybean oil, sesame oil or corn oil is used.

The capsules are formulated by filling a powdery, granular or liquid pharmaceutical composition, or the like, in gelatin capsules, or the like.

Dosage forms for intravenous, subcutaneous and intramuscular administrations include injections in the forms of sterilized aqueous solutions, non-aqueous solutions, etc. As a solvent for the aqueous solution, a physiological saline solution or the like is used. As a solvent for the non-aqueous solution, for example, propylene glycol, polyethylene glycol, a vegetable oil such as olive oil, an organic ester which is acceptable for injection such as ethyl oleate or an iodized poppy oil fatty acid ester, or the like is used. To the pharmaceutical preparations for injection are optionally added an isotonizing agent, a disinfectant, a wetting agent, an emulsifier, a dispersant, a stabilizer, etc., and the preparation may be sterilized by applying an adequate treatment such as filtration through a bacterium-retaining filter, blending of a germicide or irradiation. Also, the preparation may be prepared as an aseptic solid preparation which is used by dissolving in sterilized water or a sterilized solvent for injection just prior to use. Further, a compound of the present invention may be used in the form of a clathrate compound prepared by using α, β or γ-cyclodextrin, a methylated cyclodextrin, or the like. The compound may be used also as an injection of lipoid form.

Pharmaceutical preparations for intranasal administration are supplied in the form of a liquid or powdery composition. As the base of the liquid preparation, water, saline, a phosphate buffer solution, an acetate buffer solution, or the like is used, and the liquid preparation may contain further a surfactant, an antioxidant, a stabilizer, a preservative and/or a thickener. As the base for the powdery preparation, a water-absorbent base is preferable. Examples of the water-absorbent base include polyacrylate salts such as sodium polyacrylate, potassium polyacrylate and ammonium polyacrylate; cellulose lower-alkyl ethers such as methylcellulose, hydroxyethylcellulose, hydroxypropyl-cellulose and sodium carboxymethylcellulose; and polyethylene glycol, polyvinyl pyrrolidone, amylose, pullulan, etc., which are easily soluble in water. Further, they include celluloses such as crystalline cellulose, α-cellulose and cross-linked sodium carboxymethylcellulose; starches such as hydroxypropyl starch, carboxymethyl starch, cross-linked starches, amylose, amylopectin and pectin; proteins such as gelatin, casein and sodium caseinate; gums such as gum arabic, tragacanth gum and glucomannan; and polyvinylpolypyrrolidone, cross-linked polyacrylic acid and salts thereof, cross-linked polyvinyl alcohols, etc., which are scarcely soluble in water. These compounds may be used alone or as a mixture. The powdery preparation may be further compounded with an antioxidant, a coloring agent, a preservative, a disinfectant, an antiseptic, etc. These liquid and powdery preparations can be applied, for example, by using a spraying device, etc.

For intrarectal administration, ordinary suppositories such as gelatin soft capsules are used.

The amount of an active ingredient for treating Paget's disease of bone in the present invention is individually decided, depending on the activity of disease, but generally speaking, the amount of the active ingredient is 0.00004 to 0.2 wt. %, preferably 0.0001 to 0.1 wt. %.

The dosage of the active ingredient is also decided depending on the condition of a patient, but generally speaking, it is 0.1 to 1000 μg/day, preferably about 1 to 100 μg/day. The frequency of administration is commonly 1 to 3 times/day. A preparation is preferably formulated in such a manner that these conditions are satisfied.

In addition, the present invention provides a method for screening a compound for treatment of Paget's disease of bone, comprising the step of detecting TAFII-17, TAFII-135 or DRIP-205 gene expression. More specifically, the step of detecting TAFII-17, TAFII-135 or DRIP-205 gene expression comprises the steps of;

(a) incubating a compound to be tested with mononuclear cells prepared from bone mallow collected from a patient with Paget's disease of bone;

(b) extracting RNA from the cells from step (a);

(c) converting the RNA of step (b) into cDNA and amplifying TAFII-17, TAFII-135 or DRIP-205 gene; and (d) fractionating and determining the TAFII-17, TAFII-135 or DRIP-205 gene of step (c).

If necessary or preferable, the above-mentioned steps may be repeated by using mononuclear cells from person without Paget's disease, and result obtained by using mononuclear cells from a patient with Paget's disease and that from a person with Paget's disease are compared to obtain a test result.

In the above-mentioned method, the mononuclear cells are prepared by any method, and preferably prepared by a method described in Example 1. Extraction of RNA may be carried out according to a conventional procedure. Conversion of RNA to cDNA may be carried out by any conventional methods, such as transcription, for example by a transcriptase. Amplification of TAFII-17, TAFII-135 or DRIP-205 gene may be carried out by any conventional method, such as polymerase chain reaction, using for example a DNA polymerase. Fractionation and determination of the amplified TAFII-17, TAFII-135 or DRIP-205 gene may be carried out by any conventional method, for example electrophoresis. Incubation of the step (a) may be carried out in a culture solution such as α-MEM (α-Mineral Essential Media) containing serum, for 8 to 168 hours at a temperature of 20 to 40° C.

EXAMPLES

The present invention will be explained further in detail hereafter with examples; however, it is not restricted by the examples. Further, the Compound No. in each example is the Compound No. shown in the above Table 1.

The inventors of the present invention extracted vitamin D receptor-binding proteins from the extracts of nuclei of bone marrow cells from normal adults and patients with Paget's disease of bone; from the proteins, they isolated proteins which were detected only in the extract of nuclei of bone marrow cells from patents with Paget's disease of bone, and whose expression was induced specifically by 1α,25-dihydroxyvitamin $D_3$; and they determined the sequence of amino acid of the protein and confirmed that the factor is TAFII-17. It has been made clear that when the TAFII-17 gene is transduced into a mouse fibroblast NIH3T3 cell, the sensitivity to 1α,25-dihydroxyvitamin $D_3$ is enhanced several score of times compared with a mouse fibroblast NIH3T3 cell into which the TAFII-17 gene has not been transduced. Further, it has been found that the compound described in the present invention suppresses the expression of the TAFII-17 gene induced by 1α,25-dihydroxyvitamin $D_3$ in a bone marrow cells of patients with Paget's disease of bone and resultingly suppresses osteoclast formation. Based on these findings, it is thought that the compound suppressing the expression of a transcription factor to steroid hormone receptor is useful as a treating agent for Paget's disease of bone.

Example 1

Isolation of Vitamin D Receptor-binding Protein from the Extract of Nuclei of Bone Marrow Cells from Normal Adults and Patients with Paget's Disease of Bone, and Determination of Amino Acid Sequence of the Protein Mononuclear cells were fractionated from bone marrow cells of healthy normal adults and patients with Paget's disease of bone according to a method of Kurihara et al. (Endocrinology, vol. 126, 2733–2741 (1990) and Journal of Clinical Investigation, vol. 105, 606–614 (2000)). Briefly, bone marrow cells were obtained from normal adults and patients with Paget's disease of bone, a mononuclear cell fraction was collected by Hypaque-Ficoll density gradient centrifugation, the cell fraction was washed with α-Minimal Essential Media (α-MEM, GIBCO BRL; Grand Island, N.Y.) 3 times, and the cells were dispersed in α-MEM containing 10% fetal bovine serum (GIBCO BRL; Grand Island, N.Y.). This mononuclear cell suspension was seeded on 100-mm tissue culture plates, the culture plates were kept for 90 minutes at 37° C. in a 5% $CO_2$-air atmosphere, and the non-adherent cells were collected.

The collected mononuclear cells were dispersed in an α-MEM culture medium containing 20% horse serum in such a manner that the concentration became $10^6$ cells/ml, seeded on 100-mm tissue culture plates, and cultured for 48 hr at 37° C. in an incubator of a 5% $CO_2$-air atmosphere in the presence or absence of $10^{-8}$ M 1α,25-dihydroxyvitamin $D_3$. Subsequently, cells were collected by centrifuge and subjected to cell lysis using a lyzing buffer, and an extract of nuclei was obtained from the supernatant using a centrifuge. The VDR-binding protein out of the proteins in the extract of nuclei was subjected to pull down assay using glutathione-s-transferase-VDR (GST-VDR; gift from Dr.Shigeaki Kato, University of Tokyo, Tokyo, Japan). The extracts of nuclei of bone marrow cells from patients with Paget's disease of bone and healthy normal adults were allowed to bind to GST-VDR for 2 hr at 4° C., materials bound to the GST-VDR protein were separated at first with glutathion conjugated Sepharose 4B beads (Amersham; Piscataway, N.J.), and the nucleoproteins bound to the VDR were eluted with an SDS-page buffer and fractionated by SDS-polyacrylamide gel electrophoresis according to molecular weights. The results are shown in FIG. 1.

The proteins on the gel of SDS-polyacrylamide gel electrophoresis shown in FIG. 1 were transferred to a PVDF membrane, and a protein which was detected only in the bone marrow cells from patients with Paget's disease of bone and induced to express by 1α,25-dihydroxyvitamin $D_3$, and had a molecular weight of 17 kDa was isolated.

According to a routine procedure, the amino acid sequence of the protein was determined using the 492 Precise protein sequencing system (PE-Applied Biosystems; Faster City, Calif.), and the result is shown in Table 3.

Table 3

Amino acid sequence of protein contained in an extract of nuclei of bone marrow cells from patients with Paget's disease, binding to VDR and having a molecular weight of 17 kDa $NH_2$—
MNQFGPSALINLSNFSSIKEPASTP-
PQGSMANSTAVVKIPGTPGAGGRLSPENNQVL
TKKKLQDLVREVDPNEQLDEDVEEMLL-
QIADDFJESVVTAACQLAR-
HRKSSTLEVKDVQLHLER QWNMWIPGFGSEE-
JRPYKKACTTEAHKQRMALIRKTTKK-COOH (SEO ID NO: 13)

Example 2

Isolation of TAFII-17 Gene Protein Expressed Only in an Extract of Nuclei of Bone Marrow Cells from Patients with Paget's Disease of Bone The protein having the amino acid sequence shown in Table 3 was already reported as hTAFII20(The EMBO Journal vol. 14, 1520–1531 (1995)), but the physiological functions and physiological activities of the protein have not been reported at all. The inventors of the present invention isolated the gene encoding the protein to clarify the physiological functions. That is, mononuclear cells were prepared from bone marrow of patients with Paget's disease of bone according to the method of Example 1, 1 ml of an RNAzol B solution (Tel-Test, Inc.; Friendswood, Tex.) was added to the resulting mononuclear cells, the suspension was well shaken, and the total RNA was prepared according to a routine procedure. From the total RNA, the cDNA was obtained using a reverse transcriptase (GIBCO BRI; Grand Island, N.Y.). The TAFII-17 gene in the cdNA was amplified through PCR reaction of 35 cycles each consisting of 1-min at 94° C., 1-min at 55° C. and 1-min at 72° C. using 5'-CAGCCATGGCTATGAACCAGTTTGGCCCCTCA-3' (SEQ ID NO: 14) (sense) and 5'-ATACTGCAGTTATTTCT-TGGTTGTTTTCCG-3' (SEQ ID NO: 15) (antisense) as the primers.

The TAFII-17 cDNA (500 bp) containing the entire reading frame of human TAF II-17(hTAF II-17) gene was cloned into the pcDNA3.1-Neo vector (Invitrogen; Carlsbad, Calif.). pcDNA3.1-Neo-hTAFII-17-CDS was excised from the pVp-HA2 plasmid by EcoR1 digestion. The resulting plasmid construct, pcDNA3.1-Neo-hTAFII-17-CDS, was used in Example 3.

Example 3

Enhancement of Sensitivity to 1α,25-dihydroxyvitamin $D_3$ of TAFII-17 Gene-Transduced Mouse Fibroblast NIH3T3 Cell The promoter region of the human 25-hydroxyvitamin $D_3$-24-hydroxylase gene(−186/−5), which contains two vitamin D responsive elements (VDRE) was cloned into a luciferase reporter vector pGL3-Basic Vector (Promega; Madison, Wis.). This plasmid construct was cotransfected with a β-galactosidase expression plasmid into pcDNA3.1-Neo-hTAFII-17-CDS (Example 2) or its empty vector-transfected mouse fibroblastic cell line NIH3T3 cells by lipofection (LipofectAMINE; GIBCO BRL; Grand Island, N.Y.). Sixteen hours after the transfection, vehicle (0.1% ethanol) or 1α,25-$(OH)_2D_3$ ($10^{-10}$ to $10^{-8}$ M) was added. Forty-eight hours later, the cells were harvested in the cell lysate solution provided with the luciferase assay kit (Promega; Madison, Wis.). The luciferase activities of the cell lysates were measured with the luciferase assay kit according to the manufacturer's instructions and was standardized with the β-galactosidase activities of the same cell lysates determined with a β-galactosidase enzyme assay system (Promega; Madison, Wis.). The results are shown in FIG. 2.

In TAFII-17 gene-transfected NIH3T3 cells, the expression of a 25-hydroxyvitamin $D_{3-24}$-hydroxylase gene was accelerated by the treatment with $10^{-9}$ M 1α,25-$(OH)_2D_3$ at a significant level and, further, the expression of a 25-hydroxyvitamin $D_3$-24-hydroxylase gene was extremely accelerated by the treatment with $10^{-8}$ M 1α,25-$(OH)_2D_3$. On the contrary, in empty vector-transfected NIH3T3 cells, the expression of a 25-hydroxyvitamin $D_3$-24-hydroxylase gene was hardly detected by the treatment with $10^{-9}$ M 1α,25-$(OH)_2D_3$, and the expression of a 25-hydroxyvitamin $D_3$-24-hydroxylase gene was detected only when it was treated with $10^{-8}$ M 1α,25-$(OH)_2D_3$. That is, it is shown that in TAFII-17 gene-transfected NIH3T3 cells, the sensitivity to 1α,25-$(OH)_2D_3$ has been enhanced several score of times compared with NIH3T3 cells into which the TAFII-17 gene has not been transfected.

Example 4

Supressing Effect of (23S)-25-dehydro-1α-hydroxyvitamin $D_{3-26,23}$-lactone [Compound 11, (23S Isomer)] on the Expression of TAFII-17 Gene in Bone Marrow Cells from Patients with Paget's Disease of Bone Mononuclear cells were prepared from bone marrow collected from patients with Paget's disease of bone according to a method described in Example 1. The collected mononuclear cells were dispersed in an α-MEM culture medium containing 20% horse serum in such a manner that the concentration became $3.3 \times 10^5$ cells/ml, seeded on 35-mm tissue culture plates at 3 ml/plate, and cultured for 12 hr at 37° C. in an incubator of 5% $CO_2$-air in the presence of $10^{-10}$ M 1α, 25-dihydroxyvitamin $D_3$ and $10^{-8}$ M Compound 11 (23S isomer) of the present invention singly, or in the presence of $10^{-10}$ M 1α, 25-dihydroxyvitamin $D_3$ and $10^{-8}$ M Compound 11 (23S isomer) together. Subsequently, the cells were collected by centrifuge, RNA was extracted according to a routine procedure after the addition of 1 ml of an RNAzol B solution, and the resulting RNA was converted into cDNA by using a reverse transcriptase. The TAFII-17 gene was subjected to PCR reaction of 35 cycles each consisting of 1 min at 94° C., 1 min at 55° C. and 1 min at 72° C. using 5'-CAGCCATGGCTATGAACCAGTTTG-GCCCCTCA-3' (SEQ ID NO: 14) (sense) and 5'-ATACT-GCAGTTATTTCTTGGTTGTTTTCCG-3'(SEQ ID NO: 15) (antisense) as the primers. The PCR products were fractionated by electrophoresis using 2% agarose gel. As a house-keeping gene, β-actin was subjected to PCR reaction in the same manner, and the PCR products were fractionated by electrophoresis using 2% agarose gel. The densities of the bands of the TAFII-17 gene and the β-actin gene were determined by an image analyzer. The results are shown in Table 4.

TABLE 4

Effect of compound 11 (23S isomer) on TAFII-17 gene expression induced by 1α,25-(OH)$_2$D$_3$ in bone marrow cells from patients with Paget's disease of bone

| Compounds | TAFII-17/β-actin (arbitrary units) |
|---|---|
| Vehicle | 95.95 |
| $10^{-10}$ M 1α,25-(OH)$_2$D$_3$ | 100 |
| $10^{-8}$ M Compound 11 (23S isomer) | 6.82 |
| $10^{-10}$ M 1α,25-(OH)$_2$D$_3$ + $10^{-8}$ M Compound 11 (23S isomer) | 46.89 |

Example 1 has clarified that TAFII-17 gene is completely not expressed in bone marrow cells from normal adults. On the contrarily, in bone marrow cells from patients with Paget's disease of bone, the expression of TAFII-17 gene was observed even in the case of no treatment. Accordingly, the TAFII-17 gene was considered to be expressed by the 1α,25-(OH)$_2$D$_3$ as low level as existing in the serum since it is known that $10^{-10}$ M 1α,25-(OH)$_2$D$_3$ exists in the serum of patients with Paget's disease of bone. When $10^{-8}$ M Compound 11 (23S isomer) was added to the serum of the patients, the expression of TAFII-17 gene was remarkably suppressed. Also, the expression of TAFII-17 gene whose expression had been accelerated by $10^{-10}$ M 1α,25-(OH)$_2$D$_3$ was strongly suppressed by the addition of $10^{-8}$ M Compound 11 (23S isomer).

Example 5

Suppressing Effect of Compound 11, (23S Isomer) on Osteoclast Formation in Bone Marrow Cells from Patients with Paget's Disease of Bone It was studied whether the osteoclast formation from mononuclear cells in bone marrow was suppressed when the expression of TAFII-17 gene was suppressed as shown in Example 4.

Mononuclear cells were fractionated from bone marrow cells of patients with Paget's disease of bone as described in Example 1. The collected mononuclear cells were dispersed in an α-MEM culture medium containing 20% horse serum in such a manner that the concentration became $10^6$ cells/ml, and seeded on a 96-well multiplate at 100 μl/well. The suppression effect of Compound 11 (23S isomer) on osteoclast formation in the bone marrow cells of patients with Paget's disease of bone induced by 1α,25-dihydroxyvitamin $D_3$ was evaluated as follows. Into each well, 1α,25-dihydroxyvitamin $D_3$ of various concentrations, Compound 11 (23S isomer) of various concentrations, or a combination of $10^{-10}$ M 1α,25-dihydroxyvitamin $D_3$ and Compound 11 (23S isomer) of various concentrations was added. The culture medium was replaced two times a week, and culture was continued for 3 weeks at 37° C. in an incubator of 5% $CO_2$-air. After the culture, the culture product was subjected to 23C6 antibody (antibody; gift from Dr. Michael A. Horton, Rayne Institute, Bone and Mineral Center, London, United Kingdom) alkaline phosphatase dyeing (VECTASTAIN-ABC-AP kit; Vector Laboratories, Burlingame, Calif.), and the nuclei were dyed with methyl green. Cells that were positive to 23C6 antibody and had three or more nuclei were determined as osteoclast, and the number of all osteoclasts in each well was counted. The results are shown in Table 5.

TABLE 5

Inhibiting effect of Compound 11 (23S isomer) on osteoclast formation induced by 1α,25-dihydroxyvitamin $D_3$ in bone marrow cultures from the patients with Paget's disease of bone.

| compound | concentration | osteoclast formation (average number of cells ± S.D.) |
|---|---|---|
| control (without adding test compounds) | | 47 ± 6 |
| 1α,25-dihydroxyvitamin $D_3$ | $10^{-11}$ M | 134 ± 14 |
| | $10^{-10}$ M | 180 ± 15 |
| | $10^{-9}$ M | 211 ± 25 |
| | $10^{-8}$ M | 206 ± 16 |
| | $10^{-7}$ M | 205 ± 6 |
| compound 11 (23S isomer) | $10^{-11}$ M | 29 ± 5 |
| | $10^{-10}$ M | 20 ± 4 |
| | $10^{-9}$ M | 16 ± 2 |
| | $10^{-8}$ M | 9 ± 3 |
| | $10^{-7}$ M | 8 ± 2 |
| | $10^{-6}$ M | 1 ± 1 |
| 1α,25-dihydroxyvitamin $D_3$ | $10^{-10}$ M | |
| + compound 11 (23S isomer) | $10^{-11}$ M | 170 ± 13 |
| + compound 11 (23S isomer) | $10^{-10}$ M | 155 ± 6 |
| + compound 11 (23S isomer) | $10^{-9}$ M | 125 ± 5 |
| + compound 11 (23S isomer) | $10^{-8}$ M | 63 ± 5 |
| + compound 11 (23S isomer) | $10^{-7}$ M | 14 ± 1 |
| + compound 11 (23S isomer) | $10^{-6}$ M | 1 ± 1 |

In bone marrow cells from patients with Paget's disease of bone, as little as $10^{-11}$ M 1α,25-dihydroxyvitamin $D_3$ already caused osteoclast formation, and 1α,25-dihydroxyvitamin $D_3$ stimulated osteoclast formation concentration-dependently in the range of $10^{-11}$ M to $10^{-7}$ M; however, it exhibited almost the maximum activity at $10^{-9}$ M. Compound 11 (23S isomer) did not caused any osteoclast formation at $10^{-6}$ M, and it rather inhibited the osteoclast formation even by itself. When $10^{-10}$ M 1α,25-dihydroxyvitamin $D_3$ and Compound 11 (23S isomer) of various concentrations were simultaneously added, the osteoclast formation induced by the 1α,25-dihydroxyvitamin $D_3$ was suppressed by the Compound 11 (23S isomer) concentration-dependently in the range of $10^{-11}$ M to $10^{-6}$ M. That is, it was shown that Compound 11 (23S isomer) has an activity to suppress the osteoclast formation induced by 1α,25-dihydroxyvitamin $D_3$.

The results of experiments shown above suggest that Compound 11 (23S isomer) suppresses the expression of TAFII-17 gene, the expression being induced by 1α,25-dihydroxyvitamin $D_3$; thereby, the compound attenuates the enhancement of the sensitivity of osteoclast precursor cell to 1α,25-dihydroxyvitamin $D_3$, suppresses osteoclast formation, and as the result, suppresses bone resorption. Accordingly, an agent suppressing the expression of a transcription factor to steroid hormone receptor is expected to have characteristics as a fundamental treating agent for Paget's disease of bone.

The invention claimed is:

1. A method for treating Paget's disease of bone, comprising administering to a patient a compound which inhibits expression of general transcription factor with an interactive relation to Vitamin D receptor, wherein said compound has the formula (2):

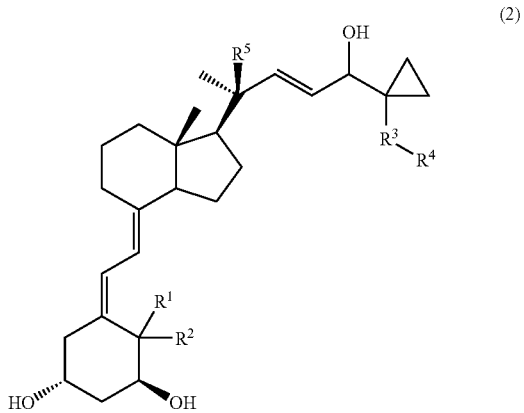

(2)

wherein $R^1$ and $R^2$ are each hydrogen or they together form an exocyclic methylene; $R^3$ is a single bond, methylene or vinylene; $R^4$ is a normal or branched $C_1$ to $C_7$ alkylcarbonyl, alkenylcarbonyl, alkoxycarbonyl or alkylaminocarbonyl; phenyl, 2-oxazolyl or 2-thiazolyl which may be substituted with a $C_1$ to $C_6$ alkyl; $R^5$ is hydrogen or methyl.

2. The method of claim 1, wherein $R^4$ is n-butylcarbonyl, n-pentylcarbonyl, n-hexylcarbonyl, n-heptylcarbonyl, 1-pentenylcarbonyl, methoxycarbonyl, ethoxycarbonyl, n-propoxycarbonyl, iso-propoxycarbonyl, 2-methylpropoxycarbonyl, n-butoxycarbonyl, t-butoxycarbonyl, n-pentyloxycarbonyl, n-hexyloxycarbonyl, n-heptyloxycarbonyl, n-butylaminocarbonyl, n-pentylaminocarbonyl, n-heptylaminocarbonyl, n-pentenylaminocarbonyl, 2-(5-butyl)oxazolyl, 2-(5-butyl)thiazolyl, 2-(4-methyl)thiazolyl or 2-(4-propyl)thiazolyl.

3. The method of claim 1, wherein $R^1$ and $R^2$ together form an exocyclic methylene; $R^3$ is a single bond; $R^4$ is n-butoxycarbonyl or 2-methylpropoxycarbonyl; $R^5$ is hydrogen.

4. The method of claim 1, wherein $R^1$ and $R^2$ together form an exocyclic methylene; $R^3$ is a single bond; $R^4$ is n-butylcarbonyl, n-pentylcarbonyl, n-heptylcarbonyl or 1-pentenylcarbonyl; $R^5$ is hydrogen.

5. The method of claim 1, wherein $R^1$ and $R^2$ together form an exocyclic methylene; $R^3$ is a single bond; $R^4$ is n-butylaminocarbonyl, n-pentylaminocarbonyl, n-heptylaminocarbonyl or 1-pentenylaminocarbonyl; $R^5$ is hydrogen.

6. The method of claim 1, wherein $R^1$ and $R^2$ together form an exocyclic methylene; $R^3$ is a single bond; $R^4$ is 2-(5-butyl)oxazolyl, 2-(5-butyl)thiazolyl, 2-(4-methyl)thiazolyl or 2-(4-propyl)thiazolyl; $R^5$ is hydrogen.

7. The method of claim 1, wherein $R^1$ and $R^2$ together form an exocyclic methylene; $R^3$ is vinylene; $R^4$ is ethoxycarbonyl or t-butoxycarbonyl; $R^5$ is hydrogen.

8. The method of claim 1, wherein $R^1$ and $R^2$ are each hydrogen; $R^3$ is a single bond; $R^4$ is n-butoxycarbonyl; $R^5$ is hydrogen.

9. The method of claim 1, wherein $R^1$ and $R^2$ are each hydrogen; $R^3$ is vinylene; $R^4$ is ethoxycarbonyl; $R^5$ hydrogen.

10. The method of claim 1, wherein $R^1$ and $R^2$ are each hydrogen; $R^3$ is a single bond; $R^4$ is 2-(4-methyl)thiazolyl; $R^5$ is hydrogen.

* * * * *

UNITED STATES PATENT AND TRADEMARK OFFICE
CERTIFICATE OF CORRECTION

PATENT NO. : 7,163,933 B2　　　　　　　　　　　　　　　　　　　　　　Page 1 of 1
APPLICATION NO. : 10/369752
DATED : January 16, 2007
INVENTOR(S) : Seiichi Ishizuka et al.

It is certified that error appears in the above-identified patent and that said Letters Patent is hereby corrected as shown below:

Title page
Under "Assignee" (item 73) please delete "Teijin Limited" and insert --Teijin Limited and Board of Reagents, The University of Texas System--

Signed and Sealed this

Sixteenth Day of December, 2008

JON W. DUDAS
*Director of the United States Patent and Trademark Office*